United States Patent
Gates et al.

(10) Patent No.: US 6,361,700 B2
(45) Date of Patent: Mar. 26, 2002

(54) METHOD AND PARTITIONING BLOOD USING POLYESTERS

(75) Inventors: Jeffrey A. Gates, West Chester, OH (US); Michael S. Sharp, Brookville, IN (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/788,967

(22) Filed: Feb. 20, 2001

Related U.S. Application Data

(62) Division of application No. 09/325,896, filed on Jun. 4, 1999, now Pat. No. 6,248,844.

(51) Int. Cl.$^7$ ......................... B01D 33/15; C08F 20/00; C08G 63/54
(52) U.S. Cl. ..................... 210/782; 525/444; 528/302; 528/303; 528/306; 528/307; 528/308; 528/308.6
(58) Field of Search ..................... 210/782; 525/444; 528/302, 303, 306, 307, 308, 308.6

(56) References Cited

U.S. PATENT DOCUMENTS

| | | | | |
|---|---|---|---|---|
| 2,736,609 A | * | 2/1956 | Vinal | 300/2 |
| 2,793,219 A | * | 5/1957 | Barrett et al. | 260/407 |
| 2,955,121 A | * | 10/1960 | Myers et al. | 260/407 |
| 4,101,422 A | * | 7/1978 | Lamont et al. | 210/84 |
| 4,148,764 A | * | 4/1979 | Lamont et al. | 260/22 D |
| 5,101,009 A | * | 3/1992 | Nakane et al. | 528/272 |
| 5,124,434 A | * | 6/1992 | O'Brien | 528/272 |
| 5,506,333 A | * | 4/1996 | O'Brien et al. | 528/272 |
| 5,556,557 A | * | 9/1996 | O'Brien et al. | 210/287 |
| 5,731,391 A | * | 3/1998 | O'Brien et al. | 525/444 |

* cited by examiner

*Primary Examiner*—Samuel A. Acquah
(74) *Attorney, Agent, or Firm*—John E. Drach; Steven J. Trzaska

(57) ABSTRACT

A polyester is provided which facilitates the separation of blood into light and heavy phases via centrifugation in a blood collection vessel. The polyester is useful as a component of a partitioning composition formulated to have appropriate specific gravity to be positioned intermediate the light and heavy blood phases during centrifugation. The polyester composition can be prepared with relative ease compared to prior art polyesters useful in blood partitioning compositions. The polyesters of this invention comprise a dicarboxylic acid member, a polymeric fatty acid, a diol member and a moiety having at least one polymerizable carbon-carbon double bond and at least one functional group capable of reacting with the ends of the polyester chain. The polyesters have a lower viscosity when synthesized and are later cured to increase their viscosity to the desired level.

19 Claims, No Drawings

METHOD AND PARTITIONING BLOOD USING POLYESTERS

This application is a Division of Ser. No. 09/325,896 filed Jun. 4, 1999 now U.S. Pat. No. 6,248,844.

BACKGROUND OF THE INVENTION

1. Field of the Invention

The present invention relates to polyesters useful for facilitating the separation of blood serum or plasma from the cellular portion of blood.

2. Description of the Related Art

The compositions of the present invention are conveniently formulated into a partitioning composition for use in a blood collection vessel in which the blood sample is subjected to centrifugation until the cellular portion and serum or plasma are completely separated.

Note that while blood is the most usual candidate for physiological separation, conceivably urine, milk, sputum, stool solutions, meconium, pus and the like could all be subject to physiological separation and assay for therapeutic agents and the subsequent discussion, while focusing on blood for clarity, is not meant to be limited to blood.

The physical and chemical properties of the partitioning composition are such that a continuous, integral seal is provided between the separated blood phases, thereby maintaining separation of the phases after centrifugation and simplifying removal of the serum or plasma from the blood collection vessel. The high volume testing of blood components in hospitals and clinics has led to the development of various devices to simplify the collection of blood samples and preparation of the samples for analysis. Typically, whole blood is collected in an evacuated, elongated glass tube that is permanently closed at one end and sealed at the other end by a rubber stopper having a diaphragm which is penetrated by the double-tipped cannula used to draw the patient's blood. After the desired quantity of blood is collected, the collection vessel is subjected to centrifugation to yield two distinct phases comprising the cellular portion of the blood (heavy phase) and the blood serum or plasma (light phase). The light phase is typically removed from the collection vessel, e.g., via pipette or decantation, for testing.

It has been proposed heretofore to provide manufactured, seal-forming members, e.g., resilient pistons, spools, discs and the like, in blood collection vessels to serve as mechanical barriers between the two separated phases. Because of the high cost of manufacturing such devices to the close tolerances required to provide a functional seal, they have been supplanted by fluid sealant compositions. Fluid sealant compositions are formulated to have a specific gravity intermediate that of the two blood phases sought to be separated, so as to provide a partition at the interface between the cellular and serum phases. Such compositions typically include a polymer base material, one or more additives for adjusting the specific gravity and viscosity of the resultant composition, and optionally, a network former. Representative fluid sealant compositions developed in the past include: styrene beads coated with an anti-coagulant; silicone fluid having silica dispersed therein; a homogeneous, hydrophobic polyester including a suitable filler, e.g., silica; a liquid alpha-olefin-dialkylmaleate, together with an aliphatic amine derivative of smectite clay or powdered silica; the reaction product of a silicone fluid with a silica filler and a network former; and a mixture of compatible viscous liquids, e.g., epoxidized vegetable oil and chlorinated polybutene, and a thixotropy-imparting agent, e.g., powdered silica, and liquid polyesters, a thixotropic gel comprising a dual resin component including poly-alpha-pinene of lower density combined with chlorinated octadecene of higher density, said gel further comprising a radiation stabilizer, a network stabilizer, a thixotropic agent and a pigment, and a gelatinous material admixed with fine resin particles having an average particle size of 0.01 to 2 microns and having an internal crosslinking density of 0.1 to 3 mmol/g.

Ideally, a commercially useful blood partitioning composition should maintain uniform physical and chemical properties for extended time periods prior to use, as well as during transportation and processing of blood samples, readily form a stable partition under normal centrifugation conditions and be relatively inert or unreactive toward the substance(s) in the blood whose presence or concentration is to be determined.

Inertness to substances sought to be determined is a particular concern when blood collection vessels are used for therapeutic drug monitoring (TDM), which is assuming an increasingly important role in drug treatment strategies. TDM enables the administration of drugs in the appropriate therapeutic ranges, established through the accumulated experience of clinicians, and consequently reduces the number of patients receiving dosage levels that are either below detection limits or toxic. Administration of drugs under TDM allows one to take into account such factors as drug tolerance developed with passage of time, presence of multiple physical disorders and synergistic or antagonistic interactions with other therapeutic agents. Among the drugs recommended for administration under TDM are those having dangerous toxicity with poorly defined clinical endpoint, steep dose-response curve, narrow therapeutic range, considerable inter-individual pharmacokinetic variability or non-linear pharmacokinetics, as well as those used in long term therapy or in the treatment of life-threatening diseases. By way of example, the evaluation of blood levels of a number of tricyclic antidepressant compounds, such as imipramine or desipramine, in relation to an empirically established therapeutic range is reported to be particularly useful in the treatment of seemingly drug-refractory depression. TDM is likewise used to monitor the dosage of anticonvulsant drugs, such as phenytoin and phenobarbital which are administered in the treatment of epilepsy, anti-tumor drugs, such as methotrexate, and other more commonly prescribed drugs, including, but not limited to digoxin, lidocaine, pentobarbital and theophylline.

Reports of studies on the effect of blood partitioning compositions on drug concentrations in serum and plasma indicate that care must be taken in the selection of polymeric materials which come into contact with the blood samples obtained for drug assay. See, for example, P. Orsulak et al., Therapeutic Drug Monitoring, 6:444–48 (1984) and Y. Bergquist et al. Clin. Chem., 30:465–66 (1984). The results of these studies show that the blood partitioning compositions provided in blood collection vessels may account for reduced serum or plasma values, as a result of drug absorption by one or more components of the composition. The reported decreases in measured drug concentrations appears to be time dependent. One report concludes that the observed decreases in drug concentrations may effectively be reduced by minimizing the interval between collection and processing. Another report recommends that blood samples be transported to the laboratory as soon as possible, with processing occurring within 4 hours. A commercially useful blood collection vessel, however, must produce accurate test results, taking into account routine clinical practices in large institutions, where collection, transportation and processing of blood samples may realistically take anywhere from about 1–72 hours.

Conventional polyester fluids are inadequate penetration barriers and therapeutic agents will diffuse into them and be partially absorbed with time, which interferes with quantitative assay for their presence. Attempts to solve this problem have centered around techniques for making the polyester itself more hydrophobic. Most therapeutic agents have high solubility parameters and associated high hydrophilicity (associated with high polarity functional groups like amines) because they must be soluble in aqueous liquids like blood, and water has a high solubility parameter. So, the direction has been to less hydrophilic, more hydrophobic, polymers to avoid the possibility of the therapeutic agents partially dissolving in a medium solubility parameter, medium polarity, polyester, and thus be more fully available in the serum phase for analysis. Imparting hydrophobic character to the polyester has been done via two main techniques. Firstly, a random polymer has been made of a diol and large quantities of a dicarboxylic acid with pendent, long ($C_9$ to $C_{13}$) olefin groups. Secondly, a random polymer has been made of a diol and large quantities of a dicarboxylic with a long olefin along its backbone, such as a $C_{36}$ dimerized fatty acid. Such polyester compositions have proved useful as functional blood partitioning compositions having reduced affinity for therapeutic agents present in blood such as phenobarbital and imipramine. See, for example, W. L. O'Brien, U.S. Pat. No. 5,124,434, the entire disclosure of which is incorporated by reference in the present specification, as if set forth herein in full.

However many of these polyesters are highly viscous and difficult to transfer to the sample collection vials. It is therefore desirable to have a material that will facilitate physiological separations but does not have the difficulties associated with transferring highly viscous liquids.

SUMMARY OF THE INVENTION

We have now quite unexpectedly discovered novel high molecular weight polyester compositions which are useful in blood separation tubes and which are derived from a short-chain dibasic acid, a polymeric fatty acid, a branched-chain saturated aliphatic diol or a mixture of diols having a branched-chain diol as the principal component and a moiety having at least one polymerizable carboncarbon double bond and at least one functional group capable of reacting with the ends of the polyester chain. These polyester compositions are advantageously employed in small amounts in blood separation tubes and form a tight seal between the light and heavy phases of the blood. The polyester compositions are not affected by contact with the blood and they do not alter the blood components. The polyesters of the invention can be synthesized having one viscosity and then later be further polymerized or cured to increase their viscosity to a desired level. The density of the polymers is such that during the blood separation ultracentrifugation procedure they locate at the interface between the serum or plasma phase and heavier cellular phase. When centrifugation is terminated the polymers form a continuous integral barrier within the assembly to prevent the phases from recombining or mixing especially when decanting or pipetting the light phase. A small but effective amount, generally 2 to 5 grams, of the polyester sufficient to form the barrier between the phases is inserted directly into the separation tube either before or after the blood sample is collected. The polyester is in the form of a liquid having a density at room temperature in the range of about 1.01 to about 1.09.

More particularly, the polyesters of the invention comprise as repeating units:

A=(—C:O—RA—O:C—) wherein A is the residue of a polymeric fatty acid, particularly preferred is the residue of $C_{36}$ dimer acid and wherein $R_A$ is an aliphatic or aromatic moiety having from about 20 to about 50 carbon atoms, preferably from about 22 to about 42 carbon atoms;

B=(—C:O—$R_B$—O:C—) wherein $R_B$ is a member selected from the group consisting of a divalent aliphatic chain of 1–46 carbon atoms, preferably of from 1–34 and more preferably of from 3 to 34 carbon atoms; a divalent cycloaliphatic chain of 3–34 carbon atoms; a divalent arylene chain of from 6–34 carbon atoms, preferably of from 9–34; a divalent alkarylene chain of from 7–34 carbon atoms, a divalent alkarylalkylene chain of from 8–34 carbon atoms and mixtures thereof;

C=(—O—$R_C$—O—) wherein $R_C$ is a member selected from the group consisting of compounds of the formula: $R_C=(CH_nR_m)_k$ wherein n=0, 1,2, or 3; R=H, $C_1$ to $C_{10}$ alkyl, $CH_2OCH_2CH_2$, $CH_2CH_2OCH_2CH_2O$ $CH_2CH_2$; m=0, 1, or 2; n+m=2; k=1 to 10; examples of the (—O—$R_c$—O—) member include, but are not limited to, 1,2 propylene glycol, 1,3 and 1,4 butanediol, 3-methyl 1,5 penanediol, diethylene glycol, triethylene glycol and the like; and D=the residue of a compound having at least one polymerizable carbon-carbon double bond and at least one functional group capable of reacting with the ends of the polyester chain.

The polyesters are broadly characterized as being inert, hydrophobic, homogeneous compositions having molecular weights of from about 1,000 to 5,000 before curing, and can achieve molecular weights of from about 5000 to 500,000 after curing, densities in the range of from about 1.015 to about 1.060 g/cm3 and 100 deg. C. viscosities (kinematic) in the range of from about 100 to about 1000 centistokes before curing, which after curing can be increased to about 500 to greater than 10,000 centistrokes. Preferably, these polyesters will have 100 degree C. viscosities (kinematic) in the range of from about 100 to about 1000 centistokes before curing, which can be increased by curing to about 3,000 to about 6,000 centistrokes, and a density between of about 1.020 to about 1.050 g/cm3. The molar ratio of the sum of $R_A$ and $R_B$ to $R_C$ is in the range from about 1:1.5 to about 1:0.67.

The polyesters of this invention comprise a polymeric fatty acid (the repeating unit A), a dicarboxylic acid member (the repeating unit B), a diol member (the repeating unit C) and a moiety (the D component) having at least one polymerizable carbon-carbon double bond and at least one functional group capable of reacting with the ends of the polyester chain. Especially useful polyesters are derived from polymeric fatty acids having 70% by weight or more $C_{36}$ dimer acid, adipic, azelaic or sebacic acids, neopentyl glycol or a mixture of neopentyl glycol and 1,2-propanediol and acrylic or methacrylic acid.

The polyesters of the present invention can be used as a functional blood partitioning composition and can optionally be formulated together with other ingredients such as suitable filler and compatible surfactant.

The polyesters of the invention can be formulated together with other ingredients, typically a suitable filler and compatible surfactant, into functional blood partitioning compositions. The density of the finished blood partitioning composition is controlled within prescribed limits, so that during centrifugation the composition becomes stably positioned at the interface between the serum or plasma phase and heavier cellular phase and, when centrifugation is terminated, forms a continuous integral barrier within the blood collection vessel to prevent the two phases from recombining or mixing, especially when decanting or pipetting the serum or plasma. The polyester blood partitioning composition can be transferred into the blood collection vessel and cured, preferably by radiation, to increase the viscosity of the polyester composition to the desired level. The polyester-based blood partitioning compositions of the invention are suited for use in TDM procedures.

DETAILED DESCRIPTION OF THE INVENTION

Other than in the operating examples, or where otherwise indicated, all numbers expressing quantities of ingredients or reaction conditions used herein are to be understood as modified in all instances by the term "about". Practice within the numerical limits stated is generally preferred. Also, throughout this description, unless expressly stated to the contrary: percent, "parts" of, and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description or of generation in situ by chemical reactions specified in the description, and does not necessarily preclude other chemical interactions among the constituents of a mixture once mixed.

The polyesters according to the invention having the repeating units as set forth above, have molecular weights from about 1,000 to about 5,000 before curing, and can achieve molecular weights from about 5000 to 500,000 after curing. The polyesters of the invention are produced in the form of liquids, having a density at room temperature in the range of from about 1.01 to about 1.09. The inertness of these polyesters makes them useful in TDM programs. The polyesters of the invention are also highly hydrophobic, exhibiting negligible water solubility. The physical and chemical properties of these polyesters are uniformly maintained over extended periods prior to use, as well as during transportation and processing of blood samples. These polyesters have the ability to undergo the ultracentrifugation necessary for the blood partitioning procedure without any detectable adverse effect.

The compositions of this invention have 100 degree C. viscosities (kinematic) in the range of from about 100 to about 1000 centistokes before curing, which after curing can be increased to about 500 to greater than 10,000 centistrokes, and a density in the range of from about 1.015 to about 1.060 g/cm3. More preferably they have a 100 degree C. kinematic viscosity in the range 3,000 to 6,000 and density in the range 1.020 to 1.050 g/cm3.

Polyesters having the above-described properties are especially useful as blood partitioning agents in blood collection vessels where they provide a continuous integral barrier or seal between the serum and clot portions of blood. In other words, the polyester completely partitions the separated phases so that the serum and cellular or clot portions are no longer in contact at any point, forming a unitary seal which firmly adheres to the inner surface of the blood collection vessel. By forming a continuous, integral barrier in this way, it is possible to easily remove the serum or plasma portion by decanting or pipetting, with the clot portion remaining undisturbed in the collection vessel.

The polyesters of this invention comprise the reaction product of a polymeric fatty acid, resulting in the repeating "A" unit; a dicarboxylic acid, resulting in the repeating "B" unit; a diol, resulting in the repeating "C" unit; and a moiety "D" having at least one polymerizable carbon-carbon double bond and at least one functional group capable of reacting with the ends of the polyester chain. The molar ratio of the sum of the dicarboxylic acid member and the polymeric fatty acid to the diol member is in the range from about 1:1.5 to about 1:0.67

The "A" unit of the invention is the residue of a polymeric fatty acid, particularly preferred is the residue of $C_{36}$ dimer acid. Suitable polymeric fatty acids have the formula:

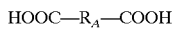

$$HOOC-R_A-COOH$$

wherein $R_A$ is an aliphatic or aromatic moiety having from about 20 to about 50 carbon atoms, preferably from about 22 to about 42 carbon atoms. The polymeric fatty acids suitable for use in the polyesters of the invention, are obtained by the polymerization of olefinically unsaturated monocarboxylic acids having from 16 to 22 carbon atoms, such as oleic acid, linolenic acid, linoleic acid, eleostearic acid and the like. Polymeric fatty acids and processes for their production are known to the art and by way of illustration reference may be had to U.S. Pat. Nos. 2,793,219 and 2,955,121, the entire disclosures of which are herein incorporated by reference. Polymeric fatty acids useful for this invention preferably will have as their principal component a $C_{36}$ dimer acid. $C_{36}$ dibasic acids are obtained by the dimerization of two moles of a $C_{18}$ unsaturated monocarboxylic acid such as oleic acid or linoleic acid or mixtures thereof (e.g., tall oil fatty acids). They typically contain 75% by weight or more $C_{36}$ dimer acid and have an acid value in the range 180–215, saponification value in the range 190–215 and neutral equivalent from 265 to 310. The dimer acids may be hydrogenated prior to use. To increase the $C_{36}$ dimer content and reduce the amount of by-product acids including unreacted mono-basic acid trimer and higher polymer acids, the polymeric fatty acid can be molecularly distilled or otherwise fractionated. Especially useful polyester compositions are obtained using polymeric fatty acids having $C_{36}$ dibasic acid contents of 85% by weight or more.

The "B" unit of the invention is the residue of a diacid. Diacids suitable for use as the dicarboxylic acid member, component "B" of the polyesters, include oxalic acid and dicarboxylic acids of the formula:

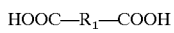

$$HOOC-R_1-COOH$$

where $R_1$ is a divalent alkylene chain having from 1 to 46 carbon atoms, and preferably is selected from the group consisting of divalent aliphatic chains of 1–34 carbon atoms and more preferably of from 3 to 34 carbon atoms; divalent cycloaliphatic chains of 3–34 carbon atoms; arylene chains of from 6–34 carbon atoms, preferably of from 9–34; alkarylene chains of from 7–34 carbon atoms, and alkaryalkylene chains of from 8–34 carbon atoms.

Suitable diacids useful in the practice of the present invention include, but are not limited to malonic acid, succinic acid, methylmalonic acid, fumaric acid, maleic acid, acetylene dicarboxylic acid, glutaric acid, ethylmalonic acid, dimethylmalonic acid, methylsuccinic acid, citraconic acid, glutasconic acid, itaconic acid, mesaconic acid, adipic acid, 2-dimethylsuccinic acid, 3methylglutaric acid, hydromuconic acid, muconic acid, pimelic acid, butylmalonic acid, diethylmalonic acid, 2-dimethylglutaric acid, 2-ethyl, 2-methylsuccinic acid, 3-methyladipic acid, cyclopentanedicarboxylic acid, suberic acid, cyclohexanedicarboxylic acid, isophthalic acid, terephthalic acid, azelaic acid, 5-norbornene-2,3-dicarboxylic acid, phenylmalonic acid, sebacic acid, camphoric acid, 1-cyclohexanediacetic acid, cyclohexylsuccinic acid, benzylmalonic acid, phenylene diacetic acid, phenylsuccinic acid, undecanedioic acid, 3phenylglutaric acid, 1,10-decanedicarboxylic acid, 4-phenylenedipropionic acid, naphthalene dicarboxylic acid, 1,11-undecanedicarboxylic acid, 1,12-dodecanedicarboxylic acid, 4-biphenyidicarboxylic acid, diphenic acid, hexadecanedioic acid, octadecanedioic acid, octadecenedioic acid, dimer acids and mixtures thereof. Especially preferred are adipic, azelaic, sebacic, and dodecanedioic acids.

It will be apparent to those skilled in the art that the various art-recognized equivalents of the aforementioned dicarboxylic acids, including lower alkylesters, anhydrides and acid chlorides thereof, may be employed in preparing the polyesters of the invention. Accordingly, as used herein, the term "acid" is intended to encompass such acid derivatives. Methyl esters are particularly advantageous for the preparation of the polyesters described herein. Mixtures of acids, anhydrides and esters may also be reacted to obtain the desired product.

The equivalents ratio of short-chain dibasic acid ("B" component of the polyester) to polymeric fatty acid ("A" component of the polyester) will range from about 4:1 to 32:1 and more preferably will be in the range 5:1 to 19:1. An essentially stoichiometric amount of the dibasic acid mixture is reacted with the branched-chain diols(s) to obtain the polyesters.

The "C" unit in the polyester of the invention is the residue of a diol. Suitable diols useful in the polyester of the invention comprise one or more esterifiable dihydric alcohol components of the formula:

$$HO-R_C-OH$$

wherein $R_C=(CH_nR_m)_k$ wherein n=0, 1 or 2; R=H, $C_1$ to $C_{10}$ alkyl, $CH_2OCH_2CH_2$, $CH_2CH_2OCH_2CH_2OCH_2CH_2$; m=0, 1 or 2; n+m=2; k=1 to 10.

Preferred diols are branched-chain aliphatic dihydric alcohols having 3 to 8 carbon atoms. Mixtures of branched-chain diols are also advantageously employed as are mixtures of a branched-chain and straight-chain aliphatic saturated diols wherein the branched-chain diol constitutes at least 50 percent by weight, and more preferably, greater than 70 percent by weight of the total diols present. When using a mixture of branched-chain and straight-chain aliphatic saturated diols, the preferred molar ratio of the respective diols is from about 1:1 to about 99:1, preferably from about 3.5:1 to about 99:1, and more preferably from about 5:1 to about 99:1. The hydroxyl groups of the diol may be either primary or secondary, however, diols having tertiary hydroxyl groups are not recommended. For the purpose of this invention a diol containing a secondary hydroxyl group is considered to be a branched-chain diol. Useful branched-chain diols include, but are not limited to, 2,2-dimethyl-1, 3-propanediol (neopentyl glycol), 2-methyl-1,3-propanediol, 3-methyl-1,5-pentanediol, 2,2,4trimethyl-1,3-pentanediol, 3-methyl-2,3-pentanediol, 1,2-propanediol, 1,3butanediol, 1,2-butanediol, 1,2-pentanediol, 1,3-pentanediol, 1,4-pentanediol and the like. Preferred diols for this invention contain from 3 to 5 carbon atoms and exceptional results are obtained using neopentyl glycol or a mixture of neopentyl glycol and 1,2-propanediol. In one of the preferred embodiments of this invention where a mixture of neopentyl glycol and 1,2-propanediol is used the equivalents ratio of the respective diols ranges from about 1:1 to about 99:1, preferably from about 3.5:1 to about 99:1, and more preferably from about 5:1 to about 99:1. Useful straight-chain (linear) aliphatic diols can have from 2 to 8 carbon atoms and include, but are not limited to, ethylene glycol, 1,3-propanediol, 1,4-butanediol, 1,6-hexanediol and the like. Additional useful diols within the scope of the invention are diethylene glycol and triethylene glycol.

Additionally, a dimer diol which is a compound of the formula:

$$HO-R_A-OH$$

wherein $R_A$ is defined as above is within the scope of useful diols for the present invention. These dimer diols are more fully described in U.S. Pat. No. 5,101,009 which is incorporated herein by reference.

D= is a residue of a compound having at least one polymerizable carbon-carbon double bond and at least one functional group capable of reacting with the ends of the polyester chain. The D moiety can be the residue of any ethylenically unsatuarated mono- or poly-functional compound capable of reacting with the ends of the polyester chain, examples of which include, but are not limited to, acrylic acid, methacrylic acid; acrylate or methacrylate esters such as methyl acrylate, ethyl acrylate, methyl methacrylate, ethyl methacrylate, particularly preferred compounds are acrylic and methacrylic alkyl esters wherein the alkyl group has from 1 to 4 carbon atoms; hydroxyalkyl acrylates and methacrylates of the following formula:

$$CH_2=CR^2-C(O)O-R^3-OH$$

wherein $R^2$ is hydrogen or methyl and $R^3$ is a linear or a branched alkylene group having from 2 to 10 carbon atoms, preferably from 2 to 6 carbon atoms, examples of which include but are not limited to, 2-hydroxyethyl acrylate, 2-hydroxypropyl acrylate, 3-hydroxypropyl acrylate, 2-hydroxybutyl acrylate, 4-hydroxybutyl acrylate, 3-hydroxypentyl acrylate, 6-hydroxynonyl acrylate, 2-hydroxyethyl methacrylate, 2-hydroxypropyl methacrylate, 3-hydroxypropyl methacrylate, 2-hydroxybutyl methacrylate, 2-hydroxypentyl methacrylate, 5-hydroxypentyl methacrylate, 7-hydroxyheptyl methacrylate and 5-hydroxydecyl methacrylate; oligomers substituted with multiple acrylate ester groups mixed with low molecular weight monofunctional, difunctional, or trifunctional acrylate monomers, for example hexanediol diacrylate; vinyl esters, such as vinyl acetate; ethylenically unsaturated monocarboxylic acids and reactive derivatives thereof (acid halide (e.g., chloride), anhydride, ester, salt) examples of which include, but are not limited to, alpha, beta-ethylenically unsaturated carboxylic acids containing from about 3 to about 8 carbon atoms; monovinyl esters of saturated and unsaturated aliphatic, monobasic and polybasic acids, such as the vinyl esters of the following acids: propionic, isobutyric, caproic, oleic, stearic, acrylic, methacrylic, crotonic, succinic, maleic, fumaric, itaconic hexahydrobenzoic, citric, tartaric, etc., as well as the corresponding allyl, methallyl, etc., esters of the aforementioned acids, the itaconic acid monoesters and diesters, such as the methyl, ethyl, butyl esters, etc.; the maleic and fumaric acid monoesters.

Conventional esterification procedures and equipment are used to obtain the polyester of the invention. The reactive components are normally added to the reaction vessel as a unit charge and the reaction mixture is then heated with agitation at a temperature from about 120 degree to about 250 degree C. for a period of time sufficient to substantially complete the esterification reaction. The reaction may be driven to completion by application of vacuum (typically 1–5 mm Hg absolute at about 150 degree to about 250 degree C.) until the desired properties are obtained. Vacuum distillation removes the final traces of water, any excess reactants and small amounts of other volatile materials present in the reaction mixture. Alternatively, all the reactive components except the moiety having at least one polymerizable carbon-carbon double bond and at least one functional group capable of reacting with the ends of the polyester chain can be added to the reaction vessel and heated until they are melted and form a homogeneous mixture at which point the moiety having at least one polymerizable carbon-carbon double bond and at least one functional group capable of reacting with the ends of the polyester chain can be added and the reaction carried out as described previously.

If improvement in color is desired, the polyester may be bleached by any of the well known and accepted bleaching methods, e.g., using hydrogen peroxide or chlorite. Alternatively, the polyester may be decolorized by filtering through a filter aid, e.g., charcoal or bleaching clay.

The rate of esterification can be enhanced by the use of known esterification catalysts. If a catalyst is used it is not necessary that it be present throughout the entire reaction. It is sometimes advantageous in order to obtain products having good color and low acid value, preferably less than 10, to add the catalyst during the final stages of the reaction. At the same time the pressure can be reduced for even better results. While the esterification can be carried out entirely at atmospheric pressure it is most desirable to reduce the pressure, typically to about 1–50 mm Hg. at about 150 degree to about 250 degree C., during the latter stages to facilitate removal of the final traces of water and excess glycol which may be present and to reduce the acid value to the desired level. Suitable esterification catalysts for enhancing the rate of esterification of free carboxyl groups include phosphoric acid, sulfuric acid, toluenesulfonic acid, methane sulfonic acid, sodium carbonate and the like. The amount of such catalyst may vary widely, but most often will be in an amount from about 0.1% to about 0.5% by weight, based on the total reactant charge. Catalysts useful for effecting ester interchange include dibutyltin diacetate, stannous oxalate, alkyl tin oxides, such as dibutyltin oxide; tetrabutyl titanate, zinc acetate and the like. These catalysts are generally employed in an amount ranging from about 0.01% to 0.05% by weight, based on the total resistant charge. When such catalysts are used, it is not necessary that they be present throughout the entire reaction. It is sometimes advantageous in order to obtain products having good color and relatively low acid value, on the order of 2 mg KOH/gm, or less, to add the catalyst during the final stages of the reaction. Upon completion of the reaction, the catalyst may be deactivated and removed by filtration or other conventional means.

Reaction solvents, such as benzene, toluene, xylene and the like may be employed for the reaction. However, the use of reaction solvents is not necessary. It is generally considered desirable to conduct the reaction without solvents since the resultant polyester can be directly used as it is obtained from the reaction vessel. A small excess (based on the equivalents of acid present) of a volatile diol component may be used if desired. The excess diol serves as the reaction medium and reduces the viscosity of the reaction mixture. The excess diol is distilled off as the esterification is carried to completion and may be recycled to the reactor, if desired. Generally, about 20% by weight excess volatile diol will suffice. The preferred volatile diol is 1,2-propanediol. It will be evident to one skilled in the art that, if the esterification is carried out in a continuous or semi-continuous manner, it will be necessary to replenish the reactants as they are consumed. Multiple vessel arrangements can be used for continuous production of these polyesters.

The polyesters of this invention can optionally be made into blood partitioning compositions by formulating with up to about 35 weight percent of an inert filler. These fillers can be added to the polyester to increase the density of the polyester composition since all of the commonly used fillers have densities greater than that of the polyester. The fillers also impart thixotropic properties to the barrier compositions. Polyesters containing small amounts of inert fillers, particularly silica, exhibit improved flow characteristics during centrifuging so that the compositions more readily located at the interface between the light and heavy phases. When centrifuging is terminated, however, the compositions return to their original state and form a highly viscous, continuous and integral barrier between the clot and serum portions. The inert fillers used are in a finely powdered state and preferably constitute from about 0.5 to 25 weight percent of the total composition. While silica, including the various amorphous form of silica, such as precipitated silica and fumed silica, and the hydrophobic silicas treated with silanes or polysiloxanes, are particularly useful with the polyesters of this invention, other inert materials such as alumina, talc and other silicates, bentonite and other naturally occurring montmorillonite-rich mineral clays can also be employed.

Preparation of blood partitioning compositions using the polyesters of the invention may be carried out in the manner described in commonly owned U.S. Pat. Nos. 4,101,422 and 4,148,764, the entire disclosures of which are incorporated by reference in the present specification, as if set forth herein in full.

The present invention also pertains to a method of partitioning blood comprising the steps of
  (i) placing an effective amount of the polyester of the invention described above into a blood collecting tube;
  (ii) curing the polyester of the invention;
  (iii) introducing the blood to be partitioned into the tube, and
  (iv) effecting the partitioning of the said blood through the action of centrifugal force.

One method by which the new compositions of this invention can be cured or converted to the infusible state, alone or in admixture with other monomers or polymers is by exposure to radiation alone or in the presence of radical generating catalysts such as benzoin, benzoin ethers, and Michler's Ketone. The free radical initiator is typically present at from about 0.01 to about 20% by weight of the polymerizable/curable components. Examples of useful radiation include ultraviolet light and ionizing radiation such as generated by X-Ray machines; electron accelerators such as van der Graaf machines, travelling wave linear accelerators, particularly of the type described in U.S. Pat. No. 2,736,609, natural and synthetic radioactive material, for example cobalt 60, etc. To ensure that the composition does not prematurely polymerize, a free radical inhibitor may be added to the polymerizable composition. Examples of suitable inhibitors include hydroquinone and the methyl ether thereof or butylated hydroxy toluene at a level of from about 5 ppm to about 2000 ppm by weight of the polymerizable components. Additives which are particularly useful in prolonging the shelf-life of the composition can also be used, e.g., ultra-violet stabilizers such as FLORSTAB® UV-II from Kromachem.

In the method of partitioning blood, according to the invention, the composition, optionally containing a photoinitiator, is placed in a blood collection tube and subsequently exposed to a radiation source until the desired viscosity is obtained. Sources of radiant energy appropriate for initiating cure of the formulations have been described extensively in the literature and are well known to those skilled in the art. These include various sources of particulate and non-particulate radiation producing wavelengths generally less than 700 nanometers. Especially useful is actinic radiation in the 180–440 nm range which can be conveniently obtained by use of one of several commercially available ultra-violet sources specifically intended for this purpose. These include low, medium and high pressure mercury vapor lamps, He-Cd and Ar lasers, xenon arc lamps, etc. Photoinitiator systems having a corresponding sensitivity to light in this wave band can be incorporated into the formulation and upon irradiation lead to the formation of reactive species capable of initiating free radical polymerization. Similarly, free radical polymerization may be induced by exposure of the formulation to an electron beam without the use of a photoinitiator. Equipment capable of generating a curtain of electrons with energies between 150 and 300 KeV is particularly suitable for this purpose and its use is well documented in the literature.

Particularly preferred sources of radiation emit electromagnetic radiation predominantly in the ultra-violet band. When such a source is used, the polymerizable composition preferably contains a photoinitiator susceptible to ultra-violet radiation, e.g., benzoin, benzoin ethers, alpha, alpha-dimethoxy-alpha-phenylacetophenone, diethoxyacetophenone, alpha-hydroxy-alpha, alpha-dimethylacetophenone, and 1-benzoylcyclohexanol.

The amount of radiation necessary to cure the composition will of course depend on the angle of exposure to the radiation, the quantity of composition placed in the collection tube, and the amount of polymerizable groups in the partitioning composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 and 420 nm (e.g., a filtered mercury arc lamp) is directed at a measured quantity of partitioning composition carried on a conveyor system which provides a rate of passage past the ultra-violet source appropriate for the radiation absorption profile of the composition (which profile is influenced by the degree of cure desired, the effective quantity of partitioning composition to be cured, and the rate of polymerization of the composition).

Determination of the extent of interaction between the polyesters of the invention and commonly monitored drugs may be carried out using well known recovery experiments and drug measurement techniques, such as, gas chromatography, gas-liquid chromatography, high-performance liquid chromatography, thin layer chromatography or immunoassay techniques, including radioimmunoassay, enzyme immunoassay, fluorescence polarization immunoassay, nephelometric assay, and the like. A variety of suitable procedures are reported in the literature. See, for example, Bergqvist, et al., supra. Such determinations may be carried out using human serum, or commercially available bovine serum, if desired.

The following examples are presented to illustrate the invention more fully, and are not intended, nor are they to be construed, as a limitation of the scope of the invention. In the examples, all percentages are on a weight basis unless otherwise indicated.

EXAMPLES

EXAMPLE 1

The reaction was carried out in a four-necked, round-bottom flask equipped with a stirrer, thermo watch, thermometer, nitrogen sweep and a medium length Vigreaux column fitted with a condenser, distillation head with thermometer and receiver. The condenser was arranged so that water and/or excess diol could be distilled from the reaction mixture at either atmospheric or reduced pressure. The reactant charge was as follows:

| | |
|---|---|
| Azelaic Acid | 640.5 g |
| C36 Dimer Acid* | 324 g |
| Neopentyl Glycol | 420 g |
| 1,2-Propanediol | 34.5 g |

*(EMPOL ® 1016, a trademark product of Henkel Corporation, Ambler PA, containing 87% $C_{36}$ dibasic acid)

*(EMPOL® 1016, a trademark product of Henkel Corporation, Ambler Pa., containing 87% $C_{36}$ dibasic acid)

The acid value was measured as 295. The flask was heated until all material was melted and appeared homogeneous. An additional charge of:

Acrylic acid 81 g was then added to the flask. The temperature of the reaction mixture was brought to about 130 to 150 degree C. while maintaining the vapor temperature at about 100 degree–120 degree C. and removing water of reaction and was heated with the vapor coming off being heated and condensed. The distillation continued until it was determined that the vapor coming from the reaction mixture was acrylic acid. The final weight was 1346 g of material. The acid value was measured at 47.8, viscosity at 100C was 139.1 centistrokes and the density at 25C was measured as 1.0201.

EXAMPLE 2

30 ml of the material made in example 1 was exposed to UV light:

| Hours of exposure | Viscosity at 100 C. |
|---|---|
| 6–8 | 254 |
| 12 | 426 |
| 16 | 755 |
| 20 | 4416 |

EXAMPLE 3

30 ml of the material made in example 1 was exposed to 7 hours of long wave UV light. The viscosity was measure at 312 and the density was measured at 1.0216.

EXAMPLE 4

The viscosity and density of a sample of unexposed material produced in example 1 was checked 12 days after it was made. The viscosity was 143 and the density was 1.0206.

What is claimed is:

1. A method of partitioning blood comprising the steps of:

(i) placing an effective amount of a polyester comprising the repeating units A, B, C and moiety D wherein:

A=(—C:O—$R_A$—O:C—) wherein A is the residue of a polymeric fatty acid and $R_A$ is an aliphatic or aromatic moiety having from about 20 to about 50 carbon atoms;

B=(—C:O—$R_B$—O:C—), wherein $R_B$ is a member selected from the group consisting of a divalent aliphatic chain of 1–34 carbon atoms; a divalent cycloaliphatic chain of 3–34 carbon atoms; a divalent arylene chain of from 6–34 carbon atoms, a divalent alkarylene chain of from 7–34 carbon atoms, a divalent alkarylalkylene chain of from 8–34 carbon atoms and mixtures thereof;

C=(—O—$R_C$—O—), wherein $R_C$ is a member selected from the group consisting of compounds of the formula: $R_C=(CH_nR_m)_k$, wherein n=0, 1,2, or 3; R=H, $C_1$ to $C_{10}$ alkyl, $CH_2OCH_2CH_2$, $CH_2CH_2OCH_2CH_2OCH_2CH_2$; m=0, 1, or 2; n+m=2; k =1 to 10; and D is the residue of a compound having at least one polymerizable carbon-carbon double bond and at least one functional group capable of reacting with the ends of the polyester chain; into a blood collecting tube;

(ii) curing the polyester;

(iii) introducing the blood to be partitioned; and (iv) effecting the partitioning of the blood through the action of centrifugal force.

2. The method of claim 1 wherein $R_B$ is a divalent aliphatic chain containing 3 to 34 carbon atoms.

3. The method of claim 1 wherein $R_B$ is a member selected from the group consisting of a divalent aliphatic chain of 3–34 carbon atoms, and said polyester exhibits a room temperature density in the range of from about 1.01 to about 1.09, a kinematic viscosity of from about 100 centistokes to about 1000 centistokes at 100 degree C. prior to the curing step (ii).

4. The method of claim 1 wherein $R_C$ is the residue of a mixture of neopentyl glycol and 1,2 propanediol.

5. The method of claim 1 wherein $R_B$ is a residue of azelaic acid, $R_C$ is the residue of a mixture of neopentyl glycol and 1,2 propanediol.

6. The method of claim 1 wherein the molar ratio of the sum of $R_A$ and $R_B$ to $R_C$ is in the range from about 1:1.5 to about 1:0.67.

7. The method of claim 1 wherein the molar ratio of the sum of $R_A$ and $R_B$ to $R_C$ is in the range from about 1:1.5 to about 1:0.67, wherein said $R_C$ member is comprised of the residue of a first dihydric alcohol component and the residue of a second dihydric alcohol component wherein the first dihydric component is a branched-chain aliphatic saturated diol and the second dihydric component is a straight-chain aliphatic saturated diol, wherein the branched-chain diol constitutes at least 50 percent by weight of the total diols present.

8. The method of claim 7 wherein the molar ratio of the first dihydric alcohol component and the second dihydric alcohol component is from about 5:1 to about 99:1.

9. The method of claim 1 wherein the polyester is cured using a source of radiation.

10. The method of claim 9 wherein the polyester has a kinematic viscosity of between about 1000 to about 6000 centistokes at 100 degree C after the curing step.

11. The method of claim 9 wherein the source of radiation is selected from the group consisting of ultraviolet light, ionizing radiation; electron accelerators, natural and synthetic radioactive material and combinations thereof.

12. The method of claim 1 wherein the polyester comprises about one mole of a dicarboxylic acid member and one mole of a diol member wherein said acid member is comprised of a first dicarboxylic acid component having 36 carbon atoms, and a second dicarboxylic acid component is selected from the group consisting of compounds with two carboxylic acids moieties linked by an aliphatic chain of 1–34 carbon atoms, a cycloaliphatic chain of 3–34 carbon atoms, an arylene chain of from 6–34 carbon atoms, an alkarylene chain of from 7–34 carbon atoms, and an alkarylalkylene chain of from 8–34 carbon atoms, or mixtures thereof; and wherein said diol member is comprised of a first dihydric alcohol component and a second dihydric alcohol component, each dihydric alcohol component being independently selected from compounds having the formula C=the group (—O—$R_C$—O—) from a dihydric alcohol wherein $R_C$ is a member selected from the group consisting of compounds of the formula:

$R_C=(CH_nR_m)_k$ wherein n=0, 1,2, or 3; R=H, $C_1$ to $C_{10}$ alkyl, $CH_2OCH_2CH_2$, $CH_2CH_2OCH_2CH_2OCH_2CH_2$; m=0, 1, or 2; n+m=2; k=1 to 10.

13. The method of claim 12 wherein the second dicarboxylic acid member is azelaic acid, the first dihydric alcohol is neopentyl glycol and the second dihydric alcohol component is 1,2 propanediol.

14. The method of claim 12 wherein in the polyester the molar ratio of the dicarboxylic acid member to the diol member is in the range from about 1:1.5 to about 1:0.67.

15. The method of claim 12 wherein in the polyester the molar ratio of the first dihydric alcohol component to the second dihydric alcohol component is in the range of from about 5:1 to about 99:1.

16. The method of claim 12 wherein in the polyester the molar ratio of the first dicarboxylic acid component to the second dicarboxylic acid component is in the range of from about 1:4 to about 1:32.

17. The method of claim 12 wherein the polyester is cured using a source of radiation.

18. The method of claim 12 wherein the polyester has a kinematic viscosity of between about 1000 to about 6000 centistokes at 100 degree C. after curing.

19. The method of claim 12 wherein the source of radiation is selected from the group consisting of ultraviolet light, ionizing radiation, electron accelerators, natural and synthetic radioactive material and combinations thereof.

* * * * *